US010563125B2

(12) United States Patent
Boogaerts et al.

(10) Patent No.: US 10,563,125 B2
(45) Date of Patent: Feb. 18, 2020

(54) STABILIZER FOR THIOL-ENE COMPOSITIONS

(71) Applicant: Allnex Belgium S.A., Drogenbos (BE)

(72) Inventors: Luc Boogaerts, Herent (BE); Steven Cappelle, Ninove (BE); Hugues Van Den Bergen, Drogenbos (BE)

(73) Assignee: ALLNEX BELGIUM S.A., Drogenbos (BE)

( * ) Notice: Subject to any disclaimer, the term of this patent is extended or adjusted under 35 U.S.C. 154(b) by 270 days.

(21) Appl. No.: 15/039,901

(22) PCT Filed: Nov. 24, 2014

(86) PCT No.: PCT/EP2014/075399
§ 371 (c)(1),
(2) Date: May 27, 2016

(87) PCT Pub. No.: WO2015/082244
PCT Pub. Date: Jun. 11, 2015

(65) Prior Publication Data
US 2017/0022414 A1    Jan. 26, 2017

(30) Foreign Application Priority Data

Dec. 2, 2013  (EP) ..................................... 13195329

(51) Int. Cl.
| C09K 15/32 | (2006.01) |
| C07C 271/22 | (2006.01) |
| C07C 69/54 | (2006.01) |
| C09K 15/08 | (2006.01) |
| C09K 15/06 | (2006.01) |

(52) U.S. Cl.
CPC ............ *C09K 15/322* (2013.01); *C07C 69/54* (2013.01); *C07C 271/22* (2013.01); *C09K 15/06* (2013.01); *C09K 15/08* (2013.01)

(58) Field of Classification Search
None
See application file for complete search history.

(56) References Cited

U.S. PATENT DOCUMENTS

| 4,443,495 | A | * | 4/1984 | Morgan ................. C08G 75/02 252/502 |
| 5,208,281 | A | | 5/1993 | Glaser |
| 5,358,976 | A | | 10/1994 | Dowling et al. |
| 5,459,173 | A | | 10/1995 | Glaser et al. |
| 6,669,873 | B1 | * | 12/2003 | Smith ................. C08G 75/045 252/183.11 |
| 2007/0043205 | A1 | * | 2/2007 | Dias ..................... C08F 283/00 528/373 |

FOREIGN PATENT DOCUMENTS

| WO | 2011/155239 | 12/2011 |
| WO | 2012/126695 | 9/2012 |
| WO | 2013/135621 | 9/2013 |

OTHER PUBLICATIONS

International Search Report dated Jan. 23, 2015 in International Application No. PCT/EP2014/075399.

* cited by examiner

*Primary Examiner* — Joseph D Anthony
(74) *Attorney, Agent, or Firm* — Wenderoth, Lind & Ponack L.L.P.

(57) ABSTRACT

The present invention relates to stabilizers for thiol-ene compositions and to radiation curable thiol-ene compositions based thereon. Such radiation curable compositions can advantageously be used in inks, overprint varnishes, coatings, adhesives, for the making of 3D objects and for the making of solder resist and gel nails. Provided in particular is an inhibitor system (I) for thiol-ene compositions based on —at least one inhibitor compound (i) having a % DPPH radical scavenging activity of at least 90%, the inhibitor compound (i) being selected from substituted benzene compounds or substituted naphthalene compounds containing at least two substituents selected from the group consisting of hydroxyl groups and C1-C3 alkoxy groups bonded directly to the benzene or the naphthalene ring, —at least one acidic compound (ii) having a pKa between 1 and 3, and —at least one compound (iii) selected from the group consisting of phosphites and phosphonites, with the proviso that if the inhibitor compound (i) is a substituted benzene that it contains at least two hydroxyl groups bonded directly to the benzene ring. Also provided is an inhibitor system (II) for thiol-ene compositions based on that is based on —at least one inhibitor compound (i) having a % DPPH radical scavenging activity of at least 90%, the inhibitor compound (i) being selected from substituted benzene compounds or substituted naphthalene compounds containing at least two substituents selected from the group consisting of hydroxyl groups and C1-C3 alkoxy groups bonded directly to the benzene or the naphthalene ring, —at least one compound (iv) selected from the group consisting of spirophosphites, and —optionally, at least one acidic compound (ii) having a pKa between 1 and 3, and with the proviso that if the inhibitor compound (i) is a substituted benzene that it contains at least two hydroxyl groups bonded directly to the benzene ring.

8 Claims, No Drawings

STABILIZER FOR THIOL-ENE COMPOSITIONS

The present invention relates to stabilizers for thiol-ene compositions and to radiation curable thiol-ene compositions based thereon. Such radiation curable compositions can advantageously be used for making gel nails, inks, coatings, adhesives, for making of 3D objects by stereolithography or 3D printing, and for the making of solder resist.

Thiol-ene compositions exhibit many advantages such as rapid polymerization rates, minimal oxygen inhibition, high conversion levels and lower shrinkage compared to an acrylate polymerization. They have one drawback though: it is difficult to stabilize them, especially to attain long-term shelf stability. All thiol-ene reactions exhibit spontaneous dark reactions, yielding polymers (oligomers) in the absence of an initiator unless an efficient inhibitor is being added.

The use of suspected carcinogenic compounds like N-PAL (tris(n-nitroso-n-phenylhydroxylamine)aluminum) is excluded as stabilizers. For some applications such as gel nails, conventional phenolic inhibitors like p-methoxy phenol (MeHQ) can be used only in limited amounts.

There is hence a demand for new acceptable and efficient thiol-ene stabilizer systems for such applications.

WO 2011/155239 relates to the use of stabilizers for thiol-ene compositions based on a substituted naphthalene compound containing at least two substituents selected from the group consisting of hydroxyl groups and/or alkoxy groups. 4-methoxy-1-naphthol (4M1N) is listed.

It has been found however that the use of 4M1N alone has limited stabilizing effect in thiol-ene compositions based on primary thiols such as 3-mercaptopropionate and secondary thiols like 3-mercaptobutylate.

Other stabilizer systems have been proposed in the art but also these presented some drawbacks.

WO 2012/126695 relates to a photocurable thiol-ene composition that is stabilized with a phosphonic acid and a substituted benzene or naphtalene containing at least two hydroxyl groups.

U.S. Pat. No. 5,459,173 relates to a thiol-ene system that is stabilized with a phenolic compound comprising an unsaturation in combination with other phenolic antioxidants.

U.S. Pat. No. 4,443,495 relates to a heat curing process for conductive inks. Described therein is a thiol acrylate system that is stabilized with pyrogallol, phosphorous acid (H3PO3) and triphenylphosphine. Phosphines however promote the Michael-addition between thiol groups and acrylate functionalities (described in Polymer Chemistry 2010, vol. 1, no. 8, p. 1196-1204) which may lead to viscosity increase and stability issues.

It is an object of the invention to provide inhibitor systems that permit to obtain radiation curable thiol-ene compositions, more in particular radiation curable thiol (meth) acrylate compositions that are stable, exhibit a long shelf and pot life resulting in a limited increase of the viscosity during the storage time.

It is another object of the invention to provide inhibitor systems that permit to obtain radiation curable thiol-ene compositions, more in particular radiation curable thiol (meth)acrylate compositions with a long term shelf stability both at room temperature (25° C.) and at elevated temperatures (e.g. 60° C.).

It is yet another object of the invention to provide inhibitor systems that permit to obtain radiation curable thiol-ene compositions, more in particular radiation curable thiol (meth)acrylate compositions with high reactivity and photosensitivity, that produce after curing 3D objects characterized by low shrinkage and brittleness and high notch impact strength.

It is yet a further object of the invention to provide inhibitor systems that are capable of stabilizing radiation curable thiol-ene compositions, more in particular radiation curable thiol (meth)acrylate compositions that contain substantial amounts of thiol compounds.

Provided in the invention is an inhibitor system (I) for thiol-ene compositions, more in particular for thiol (meth) arylate compositions, based on

- at least one inhibitor compound (i) selected from substituted benzene compounds or substituted naphthalene compounds containing at least two substituents selected from the group consisting of hydroxyl groups and C1-C3 alkoxy groups bonded directly to the benzene or the naphthalene ring,
- at least one acidic compound (ii) having a pKa between 1 and 3, and
- at least one compound (iii) selected from the group consisting of phosphites and phosphonites, with the proviso that if the inhibitor compound (i) is a substituted benzene that it contains at least two hydroxyl groups bonded directly to the benzene ring.

The hydroxyl and C1-C3 alkoxy substituents present on the benzene or the naphthalene ring are typically present in para or ortho positions.

Preferably the C1-C3 alkoxy group is a methoxy group or an ethoxy group. Most preferably the C1-C3 alkoxy group is a methoxy group.

Provided in particular is hence an inhibitor system (I) for thiol-ene compositions, more in particular for thiol (meth) acrylate compositions, based on

- at least one inhibitor compound (i) selected from the group consisting of (ia) substituted benzene compounds containing at least two hydroxyl groups bonded directly to the benzene ring and (ib) substituted naphthalene compounds containing at least one hydroxyl and at least one methoxy group bonded directly to the naphthalene ring,
- at least one acidic compound (ii) having a pKa between 1 and 3, and
- at least one compound (iii) selected from the group consisting of phosphites and phosphonites.

By "based on" is meant in particular "comprising" and more in particular "consisting essentially of". Advantageously, compounds (ii) are different from compounds (i). Advantageously, compounds (iii) are different from compounds (i) and (ii).

It has been found that in particular inhibitor compounds (i) having a % DPPH (2,2-diphenyl-1-picrylhydrazyl) radical scavenging activity of at least 90% are highly suitable for use in the present invention.

In the present invention, the % DPPH (2,2-diphenyl-1-picrylhydrazyl) radical scavenging activity is one that is measured as described in Ali et al, Chemistry Central Journal 2013, 7: 53, "Structural features, kinetic and SAR study of radical scavenging and antioxidant activities of phenolic and anilic compounds".

The 2,2-diphenyl-1-picrylhydrazyl (DPPH) radical scavenging ability herein is measured according to Brand-Williams, Cuvelier, & Berset, Food Sci Technol 1995, 28: 25-30, "Use of a free radical method to evaluate antioxidant activity".

More in particular: The examined inhibitor compound (25 µL, 5 mM) or 25 µL methanol (as a control) with 2.5 ml 0.004% DPPH in methanol (0.1 mM), are mixed. The solution is incubated for 20 min at room temperature before reading the absorbance (A) at 517 nm against methanol as blank. The inhibitory percentage of DPPH of the tested compound (Exp) is then calculated according to the following equation:

$$\text{DPPH radical scavenging activity} = 100 - ((A_{517} \text{ exp} / A_{517} \text{ control}) \times 100)$$

Typically inhibitor compounds (i) of the invention are selected from one or more of: 4-methoxy-1-naphthol (4M1N), catechol, ter-butyl catechol, hydroquinone, gallic acid and more preferably their esters (such as ethyl gallate, propyl gallate, octyl gallate or dodecyl gallate), pyrogallol, 2,4,5-trihydroxybutyrophenone (THBP). Preferred are 4-methoxy-1-naphthol, pyrogallol, the esters of gallic acid (such as ethyl gallate, propyl gallate, octyl gallate or dodecyl gallate), 2,4,5-trihydroxybutyrophenone (THBP), and mixtures thereof (of any of these). Most preferred are 4-methoxy-1-naphthol and/or the esters of gallic acid such as propyl gallate.

In an embodiment of the invention an inhibitor component (i) is used that comprises 4-methoxy-1-naphthol and/or propyl gallate.

In one embodiment of the invention, the inhibitor component (i) comprises 4-methoxy-1-naphthol. In a variant of this embodiment, 4-methoxy-1-naphthol is used in combination with one or more other inhibitor compounds (i) of the invention. In an embodiment of the invention for instance a mixture of 4-methoxy-1-naphthol with one or more of catechol, ter-butylcatechol, hydroquinone, esters of gallic acid (such as propyl gallate) and 2,4,5-trihydroxybutyrophenone can be used.

In another embodiment of the invention, the inhibitor component (i) comprises propyl gallate. In a variant of this embodiment, propyl gallate is used in combination with one or more other inhibitor compounds (i) of the invention. In an embodiment of the invention for instance a mixture of propyl gallate with one or more of 4-methoxy-1-naphthol, catechol, ter-butylcatechol, hydroquinone, other esters of gallic acid and 2,4,5-trihydroxybutyrophenone can be used.

In a particular embodiment of the invention, inhibitor compounds (i) are selected from 4-methoxy-1-naphthol and/or propyl gallate. In a variant of this embodiment the inhibitor compound (i) is 4-methoxy-1-naphthol. In another variant of this embodiment the inhibitor compound (i) is propyl gallate.

Compounds (ii) in the framework of the invention advantageously are acidic compounds having a pKa between 1 and 3. In case of polyprotic acids, it is the pKa1 that is to be taken into account. In other words, in case of polyprotic acids the pKa1 is between 1 and 3.

A few examples of suitable compounds (ii) include: phosphoric acid (pKa1=2.12) and their esters such as dibutylphosphoric acid (pKa1=1.72), EBECRYL® 168 or EBECRYL® 170; oxalic acid (pKa1=1.27); and phenylphosphonic acid (pKa=1.85). Stronger acids like PTSA (p-toluene sulphonic acid, pKa=−2.8) or weaker acids like acrylic acid (pKa=4.25) proved not efficient. Preferably the pKa (or pKa1 in case of polyprotic acids) is at least 1.1 Most preferably the pKa (or pKa1 in case of polyprotic acids) is at most 2.9.

Particularly preferred acidic compounds (ii) are oxalic acid, phosphoric acid and/or the esters of phosphoric acid (in particular the mono and di esters). Especially preferred are oxalic acid and/or the esters of phosphoric acid (in particular the mono and di esters). Most preferred are oxalic acid and/or the mono or di esters of phosphoric acid like dibutylphosphoric acid and EBECRYL® 168 or EBECRYL® 170.

Compounds (iii) in the framework of the present invention are advantageously selected from phosphites and/or phosphonites. Examples of suitable compounds (iii) are described in H. Zweifel (Ed) Plastics Additives Handbook, 5th edition, Hanser Publishers, Munich 2000. In an embodiment of the invention compounds (iii) are selected from phosphites.

Examples of suitable phosphites (iii) include but are not limited to triphenylphosphite (TPP); substituted triphenylphosphite such as tris(2,4-di-tert-butylphenyl) phosphite (available as (IRGAPHOS® 168 from Ciba/BASF); diphenyl isodecyl phosphite (available as LANKROMARK LE131 from Akcros); poly(dipropylene glycol) phenyl phosphites such as tri-dipropylene glycol phosphite (available as WESTON® 430 from Chemtura); 2-Ethylhexyl diphenyl phosphite; distearyl pentaerythritol diphosphites such as WESTON® 618F and 119F from Chemtura; Triisodecyl phosphite; phosphoric acid (2,4-di-butyl-6-methylphenyl) ethylester (available as IRGAPHOS® 38 from Ciba/BASF); or mixtures of any of these. An example of a suitable phosphonite (iii) is tetrakis(2,4-di-tert-butylphenyl)[1,1-biphenyl]-4,4'-diylbisphosphonite (available as IRGAPHOS® P-EPQ from Ciba/BASF). Preferred in this category of compounds (iii) are phosphites such as triphenylphosphite and/or substituted triphenylphosphites. An example of a substituted triphenylphosphite is tris(2,4-di-tert-butylphenyl)phosphite. In a particular embodiment of the invention, the phosphite is triphenylphosphite.

A particular sub-class of compounds (iii) are spirophosphites (iv).

Spirophosphites (iv) in general are characterized by the general Formula (I):

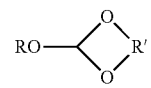

wherein R=selected from aryl and alkyl, and R'=selected from alkyl groups

Particularly interesting are compounds (iv) characterized by Formula (II)

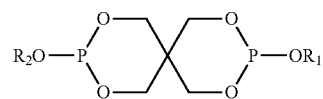

Wherein, independently, each of R1 and R2 are selected from aryl and alkyl

A particular example is

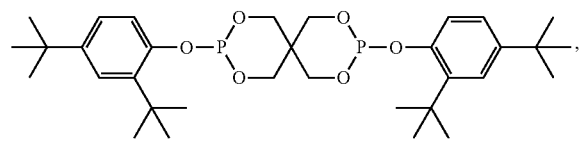 [SMILES: CC(C)(C)c1ccc(OP2OCC3(CO2)COP(Oc2ccc(C(C)(C)C)cc2C(C)(C)C)OC3)c(C(C)(C)C)c1]

also known as bis(2,4-di-tert-butylphenyl)pentaerythritol diphosphite (available as ULTRANOX® 626 from Chemtura).

In an embodiment of the invention compounds (iii) are selected from spirophosphites. Suitable spirophosphites (iv) are e.g. 2,4,6 tri-t-butylphenyl-2-butyl-2-ethyl-1,3-propanediolphosphite (available as ULTRANOX® 641 from Chemtura), bis(2,4-di-tert-butylphenyl)pentaerythritol diphosphite (available as ULTRANOX® 626 from Chemtura) and distearyl pentaerythritol diphosphite (=3,9-bis(octadecyloxy)-2,4,8,10-tetraoxa-3,9-diphosphaspiro[5.5]undecane, available as WESTON® 618F from Addivant). Particular examples include tri-t-butylphenyl-2-butyl-2-ethyl-1,3-propanediolphosphite and distearyl pentaerythritol diphosphite. A preferred compound (iv) is distearyl pentaerythritol diphosphite.

Typically the inhibitor system (I) of the invention comprises at least 5% by weight of inhibitor compounds (i), relative to the total weight of the inhibitor system. Usually this amount is at least 10% by weight, more typically this amount is at least 20% by weight. Usually this amount is at most 95% by weight, more typically this amount is at most 80% by weight.

Typically the inhibitor system (I) of the invention comprises at least 5% by weight of acidic compounds (ii), relative to the total weight of the inhibitor system. Usually this amount is at least 10% by weight, more typically this amount is at least 20% by weight. Usually this amount is at most 95% by weight, more typically this amount is at most 80% by weight.

Typically the inhibitor system (I) of the invention comprises at least 5% by weight of compounds (iii), relative to the total weight of the inhibitor system. Usually this amount is at least 10% by weight, more typically this amount is at least 20% by weight. Usually this amount is at most 95% by weight, more typically this amount is at most 80% by weight.

Typically the sum of the weight percentage of compounds (i) through (iii) in the inhibitor system (I) of the invention does not exceed 100%. Usually the sum of the weight percentages of compounds (i) through (iii) equals 100%.

It was noticed that if the phosphite (iii) is a spirophosphite (iv), that the presence of the acidic compounds (ii) as described above is not mandatory.

Hence, another aspect of the invention relates to an inhibitor system (II) for thiol-ene compositions, more in particular for thiol (meth)arylate compositions, based on
- at least one inhibitor compound (i) selected from substituted benzene compounds or substituted naphthalene compounds containing at least two substituents selected from the group consisting of hydroxyl groups and C1-C3 alkoxy groups bonded directly to the benzene or the naphthalene ring,
- at least one compound (iv) selected from the group consisting of spirophosphites, and
- optionally, at least one acidic compound (ii) having a pKa between 1 and 3, with the proviso that if the inhibitor compound (i) is a substituted benzene that it contains at least two hydroxyl groups bonded directly to the benzene ring.

More in particular there is provided an inhibitor system (II) for thiol-ene compositions, more in particular for thiol (meth)arylate compositions, based on
- at least one inhibitor compound (i) selected from the group consisting of (ia) substituted benzene compounds containing at least two hydroxyl groups bonded directly to the benzene ring and (ib) substituted naphthalene compounds containing at least one hydroxyl and at least one methoxy group bonded directly to the naphthalene ring,
- at least one compound (iv) selected from the group consisting of spirophosphites, and
- optionally, at least one acidic compound (ii) having a pKa between 1 and 3.

Once more, inhibitor compounds (i) having a % DPPH (2,2-diphenyl-1-picrylhydrazyl) radical scavenging activity of at least 90% are preferred.

Suitable examples for compounds (i), (ii) and (iv) have been described above.

Typically the inhibitor system (II) of the invention comprises at least 5% by weight of inhibitor compounds (i), relative to the total weight of the inhibitor system. Usually this amount is at least 10% by weight, more typically this amount is at least 20% by weight. Usually this amount is at most 95% by weight, more typically this amount is at most 80% by weight.

Typically the inhibitor system (II) of the invention comprises at least 5% by weight of compounds (iv), relative to the total weight of the inhibitor system. Usually this amount is at least 10% by weight, more typically this amount is at least 20% by weight. Usually this amount is at most 95% by weight, more typically this amount is at most 80% by weight.

Typically the inhibitor system (II) comprises from 0 to 95% by weight of the optional acidic compounds (ii), relative to the total weight of the inhibitor system. Usually their amount, when present, is at least 5% by weight, more typically this amount is at least 10% by weight. Usually this amount is at most 95% by weight, more typically this amount is at most 80% by weight.

Typically the sum of the weight percentage of compounds (i), (ii) and (iv) in the inhibitor system (II) of the invention does not exceed 100%. Usually the sum of the weight percentages of compounds (i), (ii) and (iv) equals 100%.

The inhibitor systems of the invention are highly suitable for use in thiol-ene compositions, more in particular for use in radiation curable thiol-ene compositions.

The inhibitor systems of the invention are in particular suitable for use in thiol (meth)acrylate compositions, more in particular radiation curable thiol (meth)acrylate compositions. An aspect of the invention hence relates to the use of inhibitor systems of the invention for the stabilization of thiol (meth)acrylate compositions, more in particular radiation curable thiol (meth)acrylate compositions. By "(meth) acrylate is meant to designate acrylate, methacrylate or mixtures thereof. "Acrylates" are often preferred.

Yet another aspect of the invention relates to a thiol-ene composition (III), more in particular a thiol (meth)acrylate composition (III), comprising at least one inhibitor system as described above (any of these described above or mixtures thereof). Typically thiol-ene compositions (III) of the invention comprise at least one thiol compound (v), at least one (meth)acrylated compound (vi) and at least one inhibitor system as described above. Compounds (v) herein are different from compounds (vi). In general compounds (vi) are different from any of compounds (i), (ii), (iii), (iv) or (v). In general compounds (v) are different from any of compounds (i), (ii), (iii), (iv) or (vi).

The thiol compound (v) can be a monofunctional or a multifunctional thiol. A multifunctional thiol can be a mixture of different thiols.

Thiol compounds (v) of the invention can bear primary and/or secondary SH groups. Preferably compounds (v) bear primary SH groups.

In general compounds (v) do not bear any (meth)acrylate groups.

Useful polythiols (v) have the formula R—(SH)n, where n is at least 2, and preferably from 2 to 4, and R is an aliphatic or aromatic organic group of valence n. R may be a polymeric or non-polymeric organic group that has a valence of n and is preferably selected from polyvalent aliphatic compounds having 1 to 30 carbon atoms and optionally one to six heteroatoms of oxygen, nitrogen or sulfur, and optionally one to six ester linkages; R can also be selected from polyoxyalkylenes, polyesters, polyolefins, polyacrylates, and polysiloxanes. With respect to n, it will be recognized that mixtures of mono-, di- and higher thiols may be used and "n" may represent a non-integral average equal to at least 2. Preferred are polythiols that comprise at least three thiol groups.

A useful class of polythiols (v) includes those obtained by esterification of a polyol with a terminally thiol-substituted carboxylic acid (or derivative thereof such as esters or acyl halides) including α- or β-mercaptocarboxylic acids such as thioglycolic acid, β-mercaptopropionic acid or β-mercaptobutanoic acid.

Useful examples of compounds (v) thus obtained include ethylene glycol bis(thioglycolate), ethylene glycol bis (3-mercaptopropionate), 1,2-propylene glycol (3-mercaptopropionate), pentaerythritol tetrakis(3-mercaptopropionate), ethylene glycol bis (3-mercapto butyrate), 1,2-propylene glycol (3-mercapto butyrate), ethylene glycol bis (2-mercaptopurine isobutyrate), 1,2-propylene glycol bis (2-mercaptopurine or trimethylolpropane tris isobutyrate) (2-mercaptopurine isobutyrate), penta pentaerythritol tetrakis (3-mercapto butyrate), 1,3,5-tris (3-mercapto ethyl butyl oxy)-1,3,5-triazine-2,4,6 (1H, 3H, 5H)-trione, 1,4-bis (3-mercapto butyryl-oxy) butane, bisphenol A bis (3-mercaptopropionate), bisphenol A bis (3-mercapto butyrate), pentaerythritol tetra-(3-mercaptopropionate), pentaerythritol tetrakis(3-mercaptobutylate), trimethylolpropane tri-(3-mercaptopropionate), trimethylolpropane tris (3-mercapto butyrate), glycol di-(3-mercaptopropionate), pentaerythritol tetramercaptoacetate, trimethylolpropane trimercaptoacetate, glycol dimercaptoacetate, ethoxylated trimethylpropane tri(3-mercapto-propionate) 700 (ETTMP 700), ethoxylated trimethylpropane tri(3-mercapto-propionate) 1300 (ETTMP 1300), propylene glycol 3-mercaptopropionate 800 (PPGMP 800), propylene glycol 3-mercaptopropionate 2200 (PPGMP 2200). pentaerythritol tetrakis (3-mercaptobutylate), ethylene glycol bis(3-mercaptopropionate), trimethylolpropane tris(thioglycolate), trimethylolpropane tris(3-mercaptopropionate), pentaerythritol tetrakis(thioglycolate), all of which are commercially available.

Poly-2-mercaptoacetate, poly-3-mercaptopropionate or poly-3-mercapto butylate esters, particularly the trimethylolpropane triesters or pentaerythritol tetraesters and alkoxylated derivatives thereof are preferred.

Most preferred polythiol compounds (v) include pentaerythritol tetrakis (3-mercaptopropionate), pentaerythritol tetrakis (3-mercaptobutylate), trimethylolpropane tris (3-mercaptopropionate) and/or trimethylolpropane tris (3-mercaptobutylate).

Compounds (vi) of the invention typically are (meth)acrylated compounds.

Compounds (vi) can be monomers, oligomers and/or polymers. Typically compounds (vi) are selected from monomers and/or oligomers that are able to cure through a thiol-ene mechanism. In particular embodiments of the invention, at least one monomer (vi) and at least one oligomer (vi) are being used.

Typically (meth)acrylated compounds (vi) that are used in the invention have a molecular weight MW of between 200 and 20,000 Daltons. Usually the MW is at most 5,000 Daltons, typically at most 4,000 Daltons, and most typically at most 3,000 Daltons. Molecular weights can be measured by gel permeation chromatography using polystyrene standards but most typically they are calculated from the target molecule.

Preferably, compounds (vi) of the invention are selected from one or more of urethane (meth)acrylate oligomers (via), polyester (meth)acrylate oligomers (vib), epoxy (meth)acrylate oligomers (vic), polycarbonate (meth)acrylates (vid), polyether (meth)acrylate oligomers (vie), (meth)acrylated (meth)acrylics oligomers (vif). These compounds are well known in the art and are for instance been described in WO2013/135621.

Urethane (meth)acrylates (via) that are used in the invention typically have a functionality of between 2 and 10.

Urethane (meth)acrylates (via) typically are obtained from the reaction of at least one polyisocyanate, at least one polymerizable ethylenically unsaturated compound containing at least one (typically one) reactive group capable to react with isocyanate groups and, optionally, at least one compound containing at least two reactive group capable to react with isocyanate groups. The reactive groups capable to react with isocyanate groups typically are —OH groups. Typically urethane (meth)acrylates (via) that are used in the invention have a molecular weight MW of between 400 and 20,000 Daltons. Usually the MW is at most 5,000 Daltons, typically at most 4,000 Daltons, and most typically at most 3,000 Daltons. Molecular weights can be measured by gel permeation chromatography using polystyrene standards but most typically they are calculated from the target molecule.

Examples of suitable urethane (meth)acrylate oligomers (via) are EBECRYL® 284, EBECRYL® 294, EBECRYL® 264, EBECRYL® 210, EBECRYL® 220, EBECRYL® 230, EBECRYL® 4858, EBECRYL® 8701, EBECRYL® 8402, EBECRYL® 8405, EBECRYL® 8465, EBECRYL® 8301, and EBECRYL® 1290, EBECRYL® 1291, EBECRYL® 8415 and EBECRYL® 8602 (all available from Allnex).

These urethane (meth)acrylates (via) can be diluted in a reactive diluent or be used in combination with other (meth)acrylated compounds.

Polyester (meth)acrylates (vib) used in the invention typically are obtained from the reaction of at least one polyol and at least one ethylenically unsaturated carboxylic acid or a suitable equivalent. Examples of suitable ethylenically unsaturated carboxylic acids include (meth)acrylic acid, β-carboxyethyl(meth)acrylate, crotonic acid, iso-crotonic acid, maleic acid, fumaric acid, itaconic acid, citraconic acid, 3-(meth)acrylamido-3-methylbutanoic acid, 10-(meth)acrylamido-undecanoic acid, 2-(meth)acrylamido-2-hydroxyacetic acid, vinyl acetic acid and/or allyl acetic acid. Acrylic acid and methacrylic acid, used alone or in combination, are preferred.

Suitable polyester (meth)acrylates (vib) are for instance aliphatic or aromatic polyhydric polyols which have been totally esterified with (meth)acrylic acid and may contain a residual hydroxyl functionality in the molecule; an easy and suitable way to characterize the product is thus by measuring its hydroxyl value (mgKOH/g). Suitable are the partial or total esterification products of (meth)acrylic acid with di-, tri-, tetra-, penta- and/or hexahydric polyols and mixtures thereof. It is also possible to use reaction products of such polyols with ethylene oxide and/or propylene oxide or mixtures thereof, or reaction products of such polyols with lactones and lactides, which add to these polyols in a ring-opening reaction.

Examples of suitable polyester (meth)acrylate oligomers are fatty acid containing polyester (meth)acrylates like EBECRYL® 870, EBECRYL® 657, and EBECRYL® 450 (all available from Allnex), and polyester (meth)acrylates like EBECRYL® 800, EBECRYL® 884, EBECRYL® 885, EBECRYL® 810 and EBECRYL® 830 (all available from Allnex).

Epoxy (meth)acrylates (vic) used in the invention typically are obtained from the reaction of at least one polyepoxy compound and at least one ethylenically unsaturated carboxylic acid or a suitable equivalent. Acrylic acid and methacrylic acid, used alone or in combination, are preferred.

Examples of suitable epoxy (meth)acrylate oligomers are the di(meth)acrylate of diglycidyl ether of Bisphenol A (BADGED(M)A), and modifications thereof (see for instance EBECRYL® 3700 or EBECRYL® 600, EBECRYL® 3701, EBECRYL® 3703, EBECRYL® 3708, EBECRYL® 3720 and EBECRYL® 3639 (all available from Allnex)). Other types of epoxy acrylate oligomers include EBECRYL® 860 (epoxidized soya oil acrylate available from Allnex).

In embodiments, the (meth)acrylated monomers (ib) may be monofunctional, difunctional, trifunctional, tetrafunctional, pentafunctional or hexafunctional (meth)acrylate monomers. Representative examples of such monomers include but are not limited to: (meth)acrylic acid, ethylene glycol di(meth)acrylate, ethoxylated bisphenol A di(meth)acrylate esters, isosorbide di(meth)acrylate, tris(2-hydroxyethyl) isocyanurate tri(meth)acrylate as well as the di(meth)acrylate, alkyl (such as isobornyl, isodecyl, isobutyl, n-butyl, t-buyl, methyl, ethyl, tetrahydrofurfuryl, cyclohexyl, n-hexyl, iso-octyl, 2-ethylhexyl, n-lauryl, octyl or decyl) or hydroxy alkyl (such as 2-hydroxyethyl and hydroxy propyl) esters of acrylic acid or methacrylic acid, phenoxyethyl(meth)acrylate, nonylphenolethoxylate mono (meth)acrylate, 2-(-2-ethoxyethoxy)ethyl(meth)acrylate, 2-butoxyethyl(meth)acrylate, butyleneglycol di(meth)acrylate and tri(meth)acrylate, 1,6-hexanediol di(meth)acrylate, ethoxylated and/or propoxylated hexanediol di(meth)acrylate, ethoxylated bisphenol A diacrylate, sorbitol di(meth) acrylate, methacrylated fatty acid, glycerol tri(meth)acrylate and the ethoxylated and/or propoxylated derivatives thereof, pentaerythritol triallyl ether, Manyl isocyanurate, bisphenol A di(meth)acrylate and tri(meth)acrylate and the ethoxylated and/or propoxylated derivatives thereof, tricyclodecanedi (meth)acrylate, tricyclodecanedimethanol di(meth)acrylate, pentaerythritol di(meth)acrylate and tri(meth)acrylate and tetra(meth)acrylate and the ethoxylated and/or propoxylated derivatives thereof (e.g. EBECRYL® 40), ethylene glycol di (meth) acrylate, diethylene glycol di (meth) acrylate, triethylene glycol di (meth) acrylate, tetraethylene glycol di (meth) acrylate, propylene glycol di(meth)acrylate, tripropylene glycol di (meth) acrylate, tetramethylene glycol di (meth) acrylate, neopentyl glycol di(meth)acrylate, ethoxylated and/or propoxylated neopentylglycol di(meth)acrylate, hexamethylene glycol di(meth)acrylate, EBECRYL® 10502 (polyether tetraacrylate), 4,4'-bis(2-acryloyloxyethoxy)diphenylpropane, trimethylolpropane di (meth) acrylate, trimethylolpropane tri(meth)acrylate and the ethoxylated and/or propoxylated derivatives thereof (e.g. EBECRYL® 10501).

Typically the concentration of compounds (v) in a thiol-ene composition (III), more in particular a thiol (meth)acrylate composition (III) of the invention is at least 1% by weight, relative to the total weight of the composition. Usually this amount is at least 2% by weight, typically at least 5% by weight, more typically 10% by weight, even more typically 20% by weight. Usually this amount is at most 70% by weight, more typically at most 50% by weight, even more typically 40% by weight.

Typically the amount of compounds (vi) in the composition (III) of the invention is at least 30% by weight, relative to the total weight of the composition. Usually this amount is at least 50% by weight, more typically at least 60% by weight. Usually this amount is at most 99%, 98%, 95% by weight, more typically at most 90% by weight, even more typically 80% by weight.

Typically the ratio of (meth)acrylated compounds (vi) over thiol compounds (v) is from 95:5 to 30:70, more typically from 90:10 to 50:50. Most typically this ratio is from 80:20 to 60:40.

Typically the amount of inhibitor compounds (i) in the composition (III) of the invention is at least 10 ppm by weight, relative to the total weight of the composition. Usually this amount is at least 50 ppm by weight, usually at least 100 ppm, more typically at least 200 ppm by weight. Usually this amount is at most 5% by weight, more typically at most 2% by weight, even more typically 1% by weight, even more 0.5% by weight.

A person skilled in the art knows that he may need to adapt the amount of inhibitors to the amount of polythiols (v) present in the composition (III). If the amount of thiols (v) present is 20 wt % or more, then some of the inhibitors need to be used at an amount of 100 ppm or more. At lower amounts of thiol compounds (v), lower amounts of inhibitor compounds (i) may suffice. Typically the amount of acidic compounds (ii) in the composition (III) of the invention is at least 10 ppm, relative to the total weight of the composition. Usually this amount is at least 50 ppm, more typically at least 200 ppm. Usually this amount is at most 30% by weight, more typically at most 15% by weight, more typically 5% by weight, generally however at most 0.5% by weight. The amount of acidic compounds (ii) in particular can be relatively high when acidic adhesion promoters like EBECRYL® 168 or 170 are used as compounds (ii). In that case amounts up to 10% by weight and higher are not unusual. Typically the acid value of the composition (III) is then at most 30 mg KOH/g, preferably at most 15 mg KOH/g, usually at most 9 mg KOH/g and most typically at most 3 mg KOH/g.

Typically the amount of compounds (iii) in the composition (III) of the invention is at least 10 ppm, relative to the total weight of the composition. Usually this amount is at least 50 ppm, more typically at least 100 ppm. Usually this amount is at most 10% by weight, more typically at most 0.5% by weight.

If the at least one compound (iii) is selected from spirophosphites (iv) then the amount of compounds (iv) in the composition (III) of the invention typically is from 10 ppm to 10% by weight, more typically from 100 ppm to 1%, and the amount of acidic compounds (ii) typically from 0 to 30% by weight, more typically from 50 ppm to 5% by weight, most typically from 200 ppm to 0.5% by weight, relative to the total weight of the composition (III).

Typically compositions (III) of the invention are radiation curable compositions that usually contain at least one photoinitiator. The radical photo-initiator can be a photo initiating system comprising a combination of different photo-initiators and/or sensitizers. The photo initiating system can, however, also be a system comprising a combination of different compounds, which do not exhibit any photo initiating property when taken alone, but which co exhibit photo initiating properties when combined together.

Thiol-ene compositions (III), more in particular thiol (meth)acrylate compositions (III) of the invention typically are cured by means of actinic radiation.

Various types of actinic radiation can be used such as ultraviolet (UV) radiation, gamma radiation, and electron beam. A preferred means of radiation curing is ultraviolet radiation. Any ultraviolet light source, as long as part of the emitted light can be absorbed by the photo-initiator (system), may be employed as a radiation source, such as, a high or low-pressure mercury lamp, a cold cathode tube, a black light, Xenon lamp, an ultraviolet LED, an ultraviolet laser, and a flash light or even visible light sources.

Compositions (Ill) of the invention have several advantages over thiol-ene compositions known in the art
  They allow relatively high amounts of thiol compounds which is advantageous for the reactivity.
  The activity of inhibitor compounds (i) is less sensitive to the actual formulation.
  Long-term shelf stability can be obtained.
  They permit to obtain low viscosity compositions
  They further benefit from high polymerization rates, minimal oxygen inhibition, high conversion level and low shrinkage compared to pure acrylate polymerization Compositions (Ill) of the invention are highly suitable for use in inks (including inkjet inks), overprint varnishes (including inkjet OPVs), coating compositions, adhesives, for the making of 3 D objects by stereolithography or 3D printing and for the making of solder resist and gel nails. Hence, yet another aspect of the invention concerns inks (including inkjet inks), overprint varnishes (including inkjet OPVs), coating compositions, adhesives, solder resists and gel nail compositions comprising a thiol-ene composition or an inhibitor system as described above. Still a further aspect of the invention concerns inks, overprint varnishes, coatings, adhesives, gel nails and 3D objects prepared from a thiol-ene composition or an inhibitor system according to the invention. Compositions (iii) of the invention are further suitable for use in additive manufacturing, conformal coatings, UV putties, fiber-reinforced plastics (more in particular glass fiber composites and carbon fiber composites), paper impregnation resins, dental applications etc. As mentioned before the thiol-ene composition of the invention most typically is a thiol (meth)acrylate composition.

Yet a further aspect of the invention concerns the use of a thiol-ene composition (more in particular a thiol (meth)acrylate composition) or an inhibitor system according to the invention for the making of inks, overprint varnishes, coating compositions, adhesives, for the making of 3 D objects by stereolithography or 3D printing, and for the making of solder resist and gel nails. Other suitable uses are listed above.

Still another aspect of the invention concerns an object or a substrate, coated or printed, at least in part with a thiol-ene composition, more in particular a thiol (meth)acrylate composition according to the invention.

Yet a further aspect of the invention concerns a gel nail prepared from an inhibitor system or a thiol-ene composition (more in particular a thiol (meth)acrylate composition) as described above.

The invention is now further described in more details in the following Examples, which in no way intend to limit the invention or its applications.

EXAMPLES

Radiation curable thiol (meth)acrylate compositions are prepared by stirring all ingredients at room temperature in a suitable recipient (e.g. a brown vial, wrapped in aluminum foil). When mixtures are ready, the recipients containing the mixtures are put in an oven at 60° C. for 10 days. Mixtures are daily checked and when a gel (0-100% of bulk liquid) is observed it is reported as 'gel after X days'. When a mixture is still liquid after 10 days (NO gel), the cone-plate viscosity is measured with constant shear rate 20 1/s at 25° C. and reported in mPa·s. Amounts are in parts (g).

TABLE 1

The use of phenolic anti-oxidants (i) only

| Composition | EX1R | EX2R | EX3R | EX4R | EX5R | EX6R |
|---|---|---|---|---|---|---|
| EBECRYL LEO 10501, Tri functional acrylate - diluting oligomer (vi) | 75 | 75 | 75 | 90 | 75 | 75 |
| Pentaerythritol tetrakis (3-mercaptopropionate) (v) | 25 | 25 | 25 | 10 | | 25 |
| Pentaerythritol tetrakis (3-mecraptobutylate) (v) | | | | | 25 | |
| 4-methoxy-1-naphthol (i) | 0.025 | 0.05 | 0.1 | 0.025 | 0.1 | |
| Pyrogallol (i) | | | | | | 0.1 |
| Viscosity (mPa · s at 25° C.) at day 0 | 105 | 105 | 105 | 80 | 123 | 105 |
| Gel (after X days) | 1 | 3 | 4 | NO | 5 | 7 |
| Viscosity (mPa · s at 25° C.) at day X | / | / | / | 101 | / | / |

Comparative Examples 1R to 6R: an inhibitor system based on inhibitor compounds (i) solely proved inefficient, even for 4-methoxy-1-naphtol. In general gel formation was observed after a few days only. No true stable thiol (meth)acrylate mixtures were obtained at elevated amounts of thiol compounds (v).

TABLE 2

The combination of an acid compound (ii) with phenolic anti-oxidants (i)

| Composition | EX7R | EX8R | EX9R |
|---|---|---|---|
| EBECRYL LEO 10501, Tri functional acrylate - diluting oligomer (vi) | 75 | 75 | 75 |
| Pentaerythritol tetrakis (3-mercaptopropionate) (v) | 25 | 25 | 25 |
| 4-methoxy-1-naphthol (i) | 0.025 | 0.05 | 0.1 |
| EBECRYL 168 (ii) | 0.1 | 0.1 | 0.1 |
| Viscosity (mPa · s at 25° C.) at day 0 | 105 | 105 | 105 |
| Gel (after X days) | 1 | 1 | 1 |
| Viscosity (mPa · s at 25° C.) at day X | / | / | / |

The above shows that inhibitor systems based on an acid compound (ii) and phenolic antioxidants (i) only proved not sufficient either (Comparative Examples 7R to 9R). Again, a gel formed rapidly.

In contrast therewith inhibitor systems (I) based on compounds (i), (ii) and (iii) according to the invention significantly improved the stability of thiol (meth)acrylate compositions as shown in Table 4.

TABLE 3

The combination of phosphites (iii) with phenolic anti-oxidants (i)

| Composition | EX10R | EX11R | EX12R | EX13R | EX14R |
|---|---|---|---|---|---|
| EBECRYL LEO 10501, Tri functional acrylate - diluting oligomer (vi) | 75 | 75 | 75 | 80 | 80 |
| Pentaerythritol tetrakis (3-mercaptopropionate) (v) | 25 | 25 | 25 | 20 | 20 |
| 4-methoxy-1-naphthol (i) | 0 | 0.025 | 0.1 | 0.025 | 0.05 |
| Triphenyl phosphite (iii) | 0.1 | 0.1 | 0.1 | 0.1 | 0.1 |
| Viscosity (mPa · s at 25° C.) at day 0 | 105 | 105 | 105 | 105 | 105 |
| Gel (after X days) | 1 | 4 | 5 | 2 | 2 |
| Viscosity (mPa · s at 25° C.) at day X | / | / | / | / | / |

The above shows that an inhibitor system based on phosphites (iii) and phenolic antioxidants (i) only provided no solution either (Comparative Examples 10R to 14R). Again, gel formation was observed after a couple of days.

In contrast therewith inhibitor systems (I) based on compounds (i), (ii) and (iii) according to the invention significantly improved the stability of thiol (meth)acrylate compositions as shown in Table 4.

types of phenolic antioxidants were used, then even when used at elevated amounts, their incorporation could not prevent gel formation. More, a gel formed as early as of day 1.

The results of Table 5 below show that similar results could be obtained with other acids (ii) according to the invention (Examples 26 to 27). These results further show that acids with a pKa outside the claimed range from 1 to 3 proved inefficient. Stronger acids like PTSA (p-toluene sulphonic acid, pKa=−2.8) or weaker acids like acrylic acid (pKa=4.25) proved not very efficient (Comparative Examples 28R to 29R).

The results of Table 6 below show that inhibitor systems (II) according to the invention are very efficient as well. When spirophosphites (iv) are used then acidic compounds (ii) according to the invention are not really needed. When we compare the results obtained with Comparative Example 30R with results obtained with Example 31 according to the invention, then we see that gel formation is delayed by using an inhibitor system (II) according to the invention. When 4-methoxy-1-naphtol was used at higher amounts, even for compositions containing 25 wt % of thiols no gel formation was observed after 10 days (Example 32). For lower amounts of thiols (v) lower amounts of 4-methoxy-1-naphtol sufficed (Examples 33 and 34). The addition of acidic compounds (ii) to the thiol (meth)acrylate composition may further improve its stability.

TABLE 4

Compositions (III) of the invention are able to stabilize thiol (meth)acrylate mixtures

| Composition | EX15 | EX16 | EX17 | EX18 | EX19 | EX20R | EX21R | EX22R | EX23R | EX24R | EX25R |
|---|---|---|---|---|---|---|---|---|---|---|---|
| EBECRYL LEO 10501, Tri functional acrylate - diluting oligomer (vi) | 75 | 75 | 75 | 75 | | 75 | 75 | 75 | 75 | 75 | 75 |
| EBECRYL 1291, Hexa functional aliphatic urethane acrylate (vi) | | | | | 80 | | | | | | |
| Pentaerythritol tetrakis (3-mercaptopropionate) (v) | 25 | 25 | 25 | 25 | 20 | 25 | 25 | 25 | 25 | 25 | 25 |
| EBECRYL ® 168 (ii) | 0.05 | 0.05 | 0.05 | 0.1 | 0.05 | 0.1 | 0.05 | 0.05 | 0.05 | 0.1 | 0.1 |
| Triphenyl phosphite (iii) | 0.05 | 0.05 | 0.05 | 0.1 | 0.05 | 0.1 | 0.05 | 0.05 | 0.05 | 0.1 | 0.1 |
| 4-methoxy-1-naphthol (i) | 0.025 | 0.05 | | | 0.05 | | | | | | |
| Butylated Hydroxy Toluene | | | | | | | 0.05 | | | 0.5 | |
| Butylated Hydroxy Anisole | | | | | | | | 0.05 | | | 0.5 |
| 4-methoxyphenol | | | | | | 0.05 | | | 0.5 | | |
| Pyrogallol (i) | | | 0.05 | | | | | | | | |
| Propyl gallate (i) | | | | 0.5 | | | | | | | |
| Viscosity (mPa · s at 25° C.) at day 0 | 105 | 105 | 105 | 105 | 20800 | 105 | 105 | 105 | 105 | 105 | 105 |
| Gel (after X days) | NO | NO | NO | NO | NO | 1 | 1 | 1 | 1 | 1 | 1 |
| Viscosity (mPa · s at 25° C.) at day X | 113 | 113 | 110 | 115 | 29000 | / | / | / | / | / | / |

Compositions 15 to 19 are compositions (III) according to the invention, comprising an inhibitor system (I) according to the invention. As follows clearly from the results shown in Table 4, the addition of acidic compounds (ii) to compounds (i) and (iii) according to the invention yielded unexpected results. The stability of the thiol (meth)acrylate mixture improved significantly. No gel is formed at elevated temperatures and the viscosity increase is negligible after 10 days at 60° C. 4-methoxy-1-naphthol (an inhibitor compound (i) according to the invention) proved most efficient. Already at levels as low as 250 ppm stable thiol (meth)acrylate compositions were obtained, even at elevated thiol concentrations (v).

Comparative Examples 20R to 25R show the importance of phenolic oxidants (i) according to the invention: If other

TABLE 5

Combination of phosphites (iii), acids (ii) and phenolic anti-oxidants (i)

| Composition | Ex26 | EX27 | EX28R | Ex29R |
|---|---|---|---|---|
| EBECRYL LEO 10501, Tri functional acrylate - diluting oligomer (vi) | 75 | 75 | 75 | 75 |
| Pentaerythritol tetrakis (3-mercaptopropionate) (v) | 25 | 25 | 25 | 25 |
| Triphenyl phosphite (iii) | 0.05 | 0.05 | 0.05 | 0.05 |
| 4-methoxy-1-naphthol (i) | 0.05 | 0.05 | 0.05 | 0.05 |
| EBECRYL ® 168 (ii) | 0.05 | | | |
| Oxalic acid (ii) | | 0.05 | | |
| Acrylic acid | | | 0.05 | |
| PTSA | | | | 0.05 |

TABLE 5-continued

Combination of phosphites (iii), acids (ii) and phenolic anti-oxidants (i)

| Composition | Ex26 | EX27 | EX28R | Ex29R |
|---|---|---|---|---|
| Viscosity (mPa · s at 25° C.) at day 0 | 105 | 105 | 105 | 105 |
| Gel (after X days) | NO | NO | 9 | 1 |
| Viscosity (mPa · s at 25° C.) at day X | 113 | 110 | / | / |

TABLE 6

The use of spiro-phosphites (iv)

| Composition | Ex30R | EX31 | EX32 | EX33 | EX34 |
|---|---|---|---|---|---|
| EBECRYL LEO 10501, Tri functional acrylate - diluting oligomer (vi) | 75 | 75 | 75 | 80 | 80 |
| Pentaerythritol tetrakis (3-mercaptopropionate) (v) | 25 | 25 | 25 | 20 | 20 |
| 4-methoxy-1-naphthol (i) | 0 | 0.025 | 0.1 | 0.025 | 0.05 |
| Spiro phosphite (iv) | 0.1 | 0.1 | 0.1 | 0.1 | 0.1 |
| Viscosity (mPa · s at 25° C.) at day 0 | 105 | 105 | 105 | 94 | 94 |
| Gel (after X days) | 1 | 3 | NO | NO | NO |
| Viscosity (mPa · s at 25° C.) at day X | / | / | 115 | 105 | 105 |

The invention claimed is:

1. An inhibitor system (I) for thiol-ene compositions based on
   at least one inhibitor compound (i) having a % 2,2-diphenyl-1-picrylhydrazyl radical scavenging activity of at least 90%, the inhibitor compound (i) being selected from substituted benzene compounds or substituted naphthalene compounds containing at least two substituents selected from the group consisting of hydroxyl groups and C1-C3 alkoxy groups bonded directly to the benzene or the naphthalene ring,
   at least one acidic compound (ii) selected from the group consisting of oxalic acid, phosphoric acid, esters of phosphoric acid, and phenylphosphonic acid, and
   at least one compound (iii) selected from the group consisting of phosphites and phosphonites,
   with the proviso that if the inhibitor compound (i) is a substituted benzene that it contains at least two hydroxyl groups bonded directly to the benzene ring.

2. The inhibitor system according to claim 1, wherein the at least one inhibitor compound (i) is selected from the group consisting of (ia) substituted benzenes containing at least two hydroxyl groups bonded directly to the benzene ring and (iib) substituted naphthalenes containing at least one hydroxyl and at least one methoxy group bonded directly to the naphthalene ring.

3. The inhibitor system according to claim 1, wherein the at least one inhibitor compound (i) is selected from the group consisting of 4-methoxy-1-naphthol, catechol, tert-butyl catechol, hydroquinone, gallic acid, the esters of gallic acid, pyrogallol and 2,4,5-trihydroxybutyrophenone.

4. The inhibitor system according to claim 1, wherein the at least one inhibitor compound (i) is selected from 4-methoxy-1-naphthol and/or from the esters of gallic acid.

5. The inhibitor system according to claim 1, wherein the acidic compound (ii) is selected from oxalic acid and/or from the esters of phosphoric acid.

6. The inhibitor system according to claim 1, wherein the phosphite (iii) is selected from triphenylphosphite and/or from substituted triphenylphosphites such as tris(2,4-di-tert-butylphenyl)phosphite.

7. The inhibitor system according to claim 1, wherein the phosphite (iii) is selected from spirophosphites.

8. A process for the stabilization of thiol (meth)acrylate compositions, said process comprising incorporating the inhibitor system of claim 1 into thiol (meth)acrylate compositions.

* * * * *